United States Patent [19]

Becuwe et al.

[11] 4,097,513

[45] Jun. 27, 1978

[54] PROCESS FOR THE PREPARATION OF 2-FLUORO-2,2-DINITROETHYL ISOCYANATE

[75] Inventors: Alain G. Becuwe, Mennecy; Jean-Pierre G. Senet, Melun; Claude M. Ucciani, Vert le Petit, all of France

[73] Assignee: Societe Nationale des Poudres et Explosifs, France

[21] Appl. No.: 749,892

[22] Filed: Dec. 13, 1976

[30] Foreign Application Priority Data

Dec. 23, 1975 France .................................. 75 39426

[51] Int. Cl.$^2$ ................. C07C 118/02; C07C 119/042
[52] U.S. Cl. ...................... 260/453 PH; 260/453 AL
[58] Field of Search ................... 260/453 AL, 453 PH

[56] References Cited

U.S. PATENT DOCUMENTS 3,991,094  11/1976  Zanker .......................... 260/453 PH

OTHER PUBLICATIONS

Adolph, J. Org. Chem., vol. 37, No. 5, pp. 747–751, (1972).

*Primary Examiner*—Dolph H. Torrence
*Attorney, Agent, or Firm*—Bucknam and Archer

[57] ABSTRACT

A process for the synthesis of 2-fluoro-2,2-dinitroethyl isocyanate which comprises reacting phosgene with 2-fluoro-2,2-dinitro-ethylamine in solution at a temperature of $-15°$ – $+5°$ C to obtain 2-fluoro-2,2-dinitro-carbamyl chloride in a first step and then decomposing said carbamyl chloride in a second step at a temperature between 20° and 50° C while passing through the solution a stream of an inert anhydrous gas.

6 Claims, No Drawings

PROCESS FOR THE PREPARATION OF 2-FLUORO-2,2-DINITROETHYL ISOCYANATE

The present invention relates to isocyanates and more specifically to the novel process for the preparation of 2-fluoro-2,2-dinitroethyl isocyanate. The invention also relates to the solution of the crude product which is obtained according to the process of this application.

The chemistry of substances contaning the 2-fluoro-2,2-dinitro-ethyl group has been the subject of a great deal of experimental work in the past because of the great interest of these substances in the field of explosives and in the field of binders and energy-producing additives for propergols. For instance U.S. Pat. No. 3,560,547 describes the preparation of 2-fluoro-2,2-dinitroethyl chloroformate; U.S. Pat. No. 3,544,630 describes the preparation of 2-fluoro-2,2-dinitro-ethylamine; other secondary amines are described in U.S. Pat. No. 3,873,617; U.S. Pat. No. 3,431,290 describes 2-fluoro-2,2-dinitroethyl carbonate and this patent describes a process for the preparation of the substance which involves the reaction between phosgene and 2-fluoro-2,2-dinitro-ethanol in the presence of pyridine oxide.

With respect to 2-fluoro-2,2-dinitroethyl isocyanate, the substance is described in the publication by H. G. Adolph in the Journal of Organic Chemistry, 37 No. 5, pp. 747–751 (1972). The process described in this publication involves the reaction of 2-fluoro-2,2-dinitro-ethylamine with phosgene in the presence of pyridine followed by decomposition of the carbamyl chloride first obtained in the presence of triethylamine to give the isocyanate. Adolph has also described an alternative procedure for the direct phosgenation of 2-fluoro-2,2-dinitro-ethylamine in the presence of triethylamine, using benzene as a solvent and at normal temperature.

The procedure described by Adolph gives a yield of crude product in the range of about only 20%. Further, the solution which is obtained cannot be directly used for subsequent reactions due to the fact that both triethylamine and the hydrochloride salt are present. It is, therefore, necessary to carry out a distillation of 2-fluoro-2,2-dinitroethyl isocyanate but this distillation constitutes a disadvantage due to the little stability of the product so that the distillation is accompanied by some hazard and in any event the yield is low.

The object of this invention is to provide a novel process for the synthesis of 2-fluoro-2,2-dinitroethyl isocyanate. Another object is to provide a process which gives a solution of the substance wich may be directly used for subsequent reactions.

The crux of the present invention resides in carrying out the preparation of the isocyanate in two steps and specifically in the first step 2-fluoro2,2-dinitro-ethylamine is reacted with phosgene at a temperature between −15° and +5° C to give the corresponding carbamyl chloride. In the second step the carbamyl chloride is decomposed at a temperature between 20° and 50° C while a stream of an anyhdrous inert gas is passed through the solution.

More specifically the process according to this invention comprises carrying out the reaction in the first step between phosgene in a solution of an inert solvent and a stirred solution of 2-fluoro-2,2-dinitro-ethylamine either in the same solvent or in another inert solvent, provided the two solvents are miscible, at a temperature between −15° and +5° C. The temperature is then allowed to rise to room temperature and stirring is continued. Then in a second stage the reaction mixture is brought to a temperature between 20° and 50° C, while maintaining a stream of an anhydrous inert gas in the solution, for a period of 3–20 hours. In this manner the carbamyl chloride which is obtained in the first stage and which is in solution is decomposed.

In accordance with a preferred embodiment of the invention, one utilizes as an inert solvent substances or mixtures of substances which have a boiling point above 20° C, preferably above 40°–50° C. The reason is that in this manner the second stage of the reaction may be carried out at a temperature lower than the boiling point of the reaction mixture. It is also advantageous to provide the reaction vessel with a reflux condenser or any other equivalent device.

In accordance with an embodiment which is particularly advantageous one may carry out the reaction in dichloromethane which is a solvent convenient for the preparation and storage of 2-fluoro-2,2-dinitro-ethylamine. The solution of phosgene may be also prepared in dichloromethane but the inventors have found that it is preferable to utilize a solution of phosgene in ethyl acetate because in this manner one favors also the decomposition of the carbamyl chloride in the second stage. Instead of ethyl acetate, one may use other esters or a carbonate such as ethyl carbonate. A very important feature of the process in accordance with the present invention, in order to achieve reproducible results, resides in using an apparatus and reagents which are perfectly dry because water decomposes the intermediate carbamyl chloride as well as the final product, that is the isocyanate. It is, therefore, essential that both stages be carried out in an inert dry atmosphere.

In the first stage of the process in accordance with the present invention, the reaction is carried out at a temperature between −15° and +5° C, preferably at −10° C. The reason is that at a temperature lower than −15° C it has been found that the reaction proceeds only at such a slow rate that for all practical purposes the reaction is not industrially acceptable, but at a temperature above +5° C the yield of the reaction is lower because of the formation of symmetrical urea derivatives which are formed by reaction of the carbamyl chloride with the amine which still has not reacted.

The phosgene solution is prepared with the precautions of letting liquid phosgene flow into a solvent which has been previously cooled for instance at a temperature of −20° C. The 2-fluoro-2,2-dinitro-ethylamine is prepared in a known manner by reaction of 2-fluoro-2,2-dinitro-ethanol with ammonia.

In general, it is preferable to use an excess of phosgene so that the molar ratio of phosgene: amine is in the order 2:4, particularly if the first stage is carried out in the range of −15° and −10° C. However, this excess may be reduced up to the amount of phosgene which corresponds to the actual stoichiometric amount. It should be noted, however, that if the excess of phosgene is avoided, one obtains low yields, particularly if the reaction is carried out at a lower temperature.

The introduction of the amine solution into the solution of phosgene is preferably carried out under stirring and the actual time required for the addition is not critical and depends essentially on the quantities of reagents being used. However, the sequence of introduction of the reactants is important and it would not be advantageous to operate in the reverse order because in such a case the formation of symmetrical urea derivatives would be unavoidable.

The reaction occurs rapidly under the conditions of the temperature range specified above and it may be ascertained due to the appearance of a white precipitate. After the reaction is completed, one continues stirring and lets the reaction mixture reach room temperature and remain at room temperature preferably for a period of at least 2 hours.

The second stage of the reaction is carried out at a temperature between 20° and 50° C. At a temperature below 20° C the decomposition is too slow but at a temperature above 50° C a rapid complete degradation of the carbamyl chloride occurs without formation of the desired isocyanate.

An important feature of the process according to the present invention resides in circulating a stream of an inert anhydrous gas through the reaction mixture during the reaction. As inert gas one may use for instance, nitrogen, rare gases and carbon dioxide. The inventors have found that surprisingly, by the use of this circulation of the inert gas, it is possible to omit the use of a reagent which would serve as the acid acceptor. This finding is very important because the acid acceptors are difficult to eliminate from the final solution and may cause a decomposition of the products which have been formed particularly to give isocyanurates.

The length of time required to carry the second stage of the process is in the order of 3–20 hours, with a shorter period of time giving an incomplete reaction and a longer period of time causing the degradation and in every instance causing a lowering in the yield. The progress of the reaction may be followed by observing the progressive disappearance of the white precipitate. The length of the reaction is short the more the temperature is kept close to the upper permissable limit of 50° C.

The reaction mixture obtained after the second step has been carried out is filtered for the purpose of eliminating a small amount of the hydrochloride of 2-fluoro-2,2-dinitro-ethylamine which has formed as a fine precipitate. In this manner there is obtained a solution of 2-fluoro-2,2-dinitro-ethyl isocyanate in a solvent or a mixture of solvents depending on the solvent or solvents used in the first step of the process. This solution may be used directly in order to carry out subsequent steps.

The yield of the isocyanate is in the range of 50% and may be as high as 70%.

The product obtained according to the process described hereinabove may be identified by its infrared spectrum and also through a known derivative, ethyl (N-2-fluoro-2,2-dinitro-ethyl) carbamate which is described by Grakauskas and Baum in the Journal of Organic Chemistry, 36, 2599–2601 (1971).

The process in accordance with the present invention gives a very surprising result because one skilled in the art would not have expected that the elimination of known acid acceptors such as pyridine and triethylamine would lead under the experimental conditions of the present application to such a substantial improvement in yield. On the other hand, it is particularly advantageous to obtain a solution containing the crude product which may be used directly for subsequent reactions. Indeed 2-fluoro-2,2-dinitroethyl isocyanate is essentially useful as an intermediate in many processes. Finally it is not necessary in accordance with the present invention to separate the product by distillation, a stage which has been carried out up to the present invention but which has resulted in substantial losses of the product.

The example described hereinbelow is given by way of illustration and should not be considered as limiting the scope of the invention.

EXAMPLE

First Step

In a reaction vessel of 150 ml. capacity, carefully dried and provide with a reflux condenser, the condenser being capable of operating at −40° C, a thermometer, a stirrer and dropping funnel, one introduces 35 grams of liquid phosgene (0.35 mole) at a temperature of −20° C and 70 ml. of ethyl acetate. A solution of 2-fluoro-2,2-dinitro-ethylamine in dichloromethane, in the amount of 70 ml., is added to the vessel described hereinabove over a period of 30 minutes, while keeping the temperature in the range of −10° C. During the addition, the reaction mixture is gently stirred.

The 2-fluoro-2,2-dinitro-ethylamine is previously prepared by reaction of 0.1 mole of 2-fluoro-2,2-dinitroethanol and ammonia. One observes the formation of a white precipitate. Then one lets the reaction mixture reach room temperature of 20° C and stirring is continued for a period of 15 hours.

Second Step

The solution obtained hereinabove is then brought to a temperature of 40° C and this temperature is maintained for a period of 4 hours. During the entire reaction period a stream of dry nitrogen is passed through the solution. The dry nitrogen carries away the gaseous hydrogen chloride and the excess of phosgene initially used. After elimination of insoluble materials, essentially the hydrochloride of 2-fluoro-2,2-dinitro-ethylamine, there is obtained 80 ml. of a solution of the desired product, 2-fluoro-2,2-dinitroethyl isocyanate. The entire reaction is carried out in a atmosphere of dry nitrogen.

The infrared spectrum of the solution prepared is described hereinabove confirms the structure of the product because it exhibits an absorption band at 2280 cm-1 which is characteristic of the isocyanate group.

A derivative is prepared by placing 20 ml. of the solution of 2-fluoro-2,2-dinitroethyl isocyanate and a very small amount of dibutyl tin dilaurate in a container, adding 20 grams of ethanol, letting the reaction mixture reach the temperature of 35° C and maintaining this temperature for one hour. After allowing the solution to return to room temperature, the solvents are removed together with the excess ethanol by distillation under vacuo. The brown oil which is obtained is purified by distillation under partial vacuo. There is obtained 2.4 grams of turbid liquid which has a boiling point of 95° C at 0.2mm of mercury. The product is ethyl (N-2-fluoro-2,2 dinitroethyl) carbamate and the infrared spectrum is in total agreement with the structure of this derivative as shown hereinbelow.

| ABSORPTION BAND AT | GROUP RESPONSIBLE |
|---|---|
| 17,745 cm −1 | C = 0 of a carbamate |
| 3,460 cm −1 | N —H |
| 1,610 cm −1 | $NO_2$ |
| 850 $cm^{-1}$ | C —F |

The infrared spectrum reported hereinabove is identical to the infrared spectrum obtained by Grakauskas and Baum (loc. cit.) directly using the mixture of ethanol, ammonia and ethyl chloroformate. The authors have reported a boiling point of 85° C at a pressure of 0.1 mm. of mercury, which corresponds to the boiling point of 95° C at a pressure of 0.2 mm. of mercury reported by the applicants.

The yield in the process which leads to the preparation of the isocyanate is 43% determined on the basis of the reaction of the formation of the derivative described hereinabove, which is essentially quantitative.

What is claimed is:

1. A process for the preparation of a solution of 2-fluoro-2,2-dinitroethyl isocyanate which comprises reacting phosgene with 2-fluoro-2,2-dinitro-ethylamine in solution in the absence of an added acid acceptor at a temperature of $-15°$ – $+5°$ C to obtain 2-fluoro-2,2-dinitro-carbamyl chloride in the first step and then decomposing said carbamyl chloride in a second step in the absence of an added acid acceptor at a temperature between 20° and 50° C while passing through the solution a stream of an inert anhydrous gas.

2. The process according to claim 1 wherein in the first step a solution of phosgene is used in a first inert solvent and the solution of said 2-fluoro-2,2-dinitro-ethylamine is prepared in the same inert solvent or in another inert solvent miscible with said first solvent and the solution of the amine is kept under stirring.

3. The process according to claim 2 wherein the phosgene is dissolved in ethyl acetate and said 2-fluoro-2,2-dinitro-ethylamine is dissolved in dichloromethane.

4. The process according to claim 1 wherein after the first step, the temperature is allowed to rise to room temperature while continuing stirring.

5. The process according to claim 1 wherein the second step takes place in a period of 3–20 hours.

6. The process according to claim 1 wherein the inert gas is nitrogen or carbon dioxide or a rare gas.

* * * * *